(12) United States Patent
Kitsell et al.

(10) Patent No.: US 10,451,596 B2
(45) Date of Patent: Oct. 22, 2019

(54) SENSOR CALIBRATION SYSTEMS AND METHOD FOR A CONTROLLED ATMOSPHERE WORKSTATION

(71) Applicant: Don Whitley Scientific Limited, Bingley, West Yorkshire (GB)

(72) Inventors: Evan Jonathan Kitsell, Shipley (GB); David Boast, Shipley (GB)

(73) Assignee: Don Whitley Scientific Limited, Bingley, West Yorkshire (GB)

( * ) Notice: Subject to any disclaimer, the term of this patent is extended or adjusted under 35 U.S.C. 154(b) by 458 days.

(21) Appl. No.: 15/189,653

(22) Filed: Jun. 22, 2016

(65) Prior Publication Data

US 2016/0377584 A1 Dec. 29, 2016

(30) Foreign Application Priority Data

Jun. 24, 2015 (GB) .................... 1511140.4

(51) Int. Cl.
*B25J 21/02* (2006.01)
*G01N 33/00* (2006.01)
(Continued)

(52) U.S. Cl.
CPC .......... *G01N 33/0006* (2013.01); *B01L 1/025* (2013.01); *B08B 15/02* (2013.01);
(Continued)

(58) Field of Classification Search
CPC ............................. G01N 33/0006; B25J 21/02
See application file for complete search history.

(56) References Cited

U.S. PATENT DOCUMENTS 3,495,437 A * 2/1970 Estes ...................... G01N 21/91
324/459
4,039,933 A * 8/1977 Moran ................. G01D 18/004
324/425
(Continued)

FOREIGN PATENT DOCUMENTS

CN 104374879 A 2/2015
CN 104655567 A 5/2015
(Continued)

OTHER PUBLICATIONS

Search Report for Great Britain Application Serial No. 1511140.4, dated Mar. 3, 2016 (3 pages).
(Continued)

*Primary Examiner* — Lisa M Caputo
*Assistant Examiner* — Alex T Devito
(74) *Attorney, Agent, or Firm* — Dorsey & Whitney LLP

(57) ABSTRACT

An automated sensor calibration system and method provide for calibrating a gas sensor in-situ in a controlled atmosphere workstation. The system comprises a controller for automatically controlling the calibration system; an enclosure member movable between a first position and a second position; and a drive mechanism, operable by the controller, for moving the enclosure member between the first position and the second position. In the first position, the enclosure member is arranged in a spaced relationship from the sensor such that a sensing head of the sensor is exposed to the controlled atmosphere of the workstation. In the second position, the enclosure member is arranged in engagement with at least one surface so as to define a calibration chamber and enclose the sensing head in the calibration chamber.

22 Claims, 5 Drawing Sheets

(51) Int. Cl.
*B01L 1/02* (2006.01)
*B08B 15/02* (2006.01)
G01N 27/407 (2006.01)
G01N 27/416 (2006.01)

(52) U.S. Cl.
CPC ............ *B08B 15/026* (2013.01); *B25J 21/02* (2013.01); *B01L 2200/087* (2013.01); *B01L 2200/148* (2013.01); *B01L 2300/0663* (2013.01); *G01N 27/407* (2013.01); *G01N 27/4163* (2013.01); *G01N 33/0009* (2013.01)

(56) References Cited

U.S. PATENT DOCUMENTS

| | | | |
|---|---|---|---|
| 4,279,142 A | 7/1981 | McIntyre | |
| 4,489,590 A | 12/1984 | Hadden | |
| 4,578,986 A * | 4/1986 | Navarre | G01N 33/0031 73/1.02 |
| 4,742,708 A | 5/1988 | Porter | |

FOREIGN PATENT DOCUMENTS

| | | |
|---|---|---|
| DE | 19708052 A1 | 11/1997 |
| WO | 2013144588 A2 | 10/2013 |

OTHER PUBLICATIONS

Search Report for GB Application No. 1511140.4, dated Mar. 3, 2016 (3 pages).
Extended European Search Report for European Patent Application No. 16175511.1, dated Oct. 28, 2016 (9 pages).

* cited by examiner

SENSOR CALIBRATION SYSTEMS AND METHOD FOR A CONTROLLED ATMOSPHERE WORKSTATION

CROSS-REFERENCE TO RELATED APPLICATIONS

This application claims priority to British Patent Application No. GB 1511140.4, entitled SENSOR CALIBRATION SYSTEM AND METHOD FOR A CONTROLLED ATMOSPHERE WORKSTATION, filed Jun. 24, 2015, which is incorporated by reference herein, in the entirety and for all purposes.

FIELD

The present invention relates to a sensor calibration system and method for a controlled atmosphere workstation.

BACKGROUND

The atmosphere of a workstation may be controlled to have a certain temperature, humidity, pressure and/or chemical composition. For example, a controlled atmosphere workstation may have a normoxic, hypoxic, anoxic or anaerobic atmosphere, where the oxygen concentration is controlled.

To monitor the oxygen concentration of a controlled atmosphere, conventional workstations typically comprise an oxygen sensor. It is known that the accuracy of the oxygen sensor can deteriorate over time. Therefore, to avoid a degradation of performance, the oxygen sensor is calibrated on a regular basis.

One known way of calibrating an oxygen sensor involves removing the oxygen sensor from the workstation and conducting the calibration process remotely. However, it has been found that the removal of the oxygen sensor increases the risk of sensor damage, may cause thermal shock and lead to the formation of condensation of the sensor surface. This approach also results in significant down-time, disrupting the operation of the workstation.

In an alternative approach, calibration may involve manually calibrating an oxygen sensor whilst it remains in-situ within the workstation. However, this approach requires an operator to insert his arms into the workstation and so the size of the workstation is restricted to allow the operator to reach the oxygen sensor and manoeuvre the calibration apparatus. Human-error may occur when operating the calibration apparatus in restricted conditions and when following the complex, multi-step calibration procedure. There is also an increased risk that controlled atmosphere may escape or ambient air may enter the workstation during calibration.

SUMMARY

The present invention seeks to address and/or ameliorate the one or more calibration problems described above. The present invention seeks to provide an improved sensor calibration system and method for a controlled atmosphere workstation.

A first aspect of the present invention relates to an automated calibration system for calibrating a gas sensor arranged in-situ in a controlled atmosphere workstation.

The gas sensor may be any suitable gas sensor for monitoring the concentration of a certain gas in the controlled atmosphere of the workstation. The gas sensor may, for example, be an oxygen sensor to monitor the concentration of oxygen in the controlled atmosphere of the workstation.

By calibrating the sensor in-situ, the risk of sensor damage is reduced, the temperature of the sensor is at least substantially maintained and condensation is avoided.

The calibration system comprises automatic control means for automatically operating the calibration system with limited or no operator intervention.

By automating the calibration system, the accuracy and speed of calibration is improved, the size of the workstation is unrestricted, the risk of human-error is avoided and disruption of the controlled atmosphere is reduced. Moreover, the calibration process is significantly simplified for an operator.

The calibration system advantageously allows for the calibration of the gas sensor without compromising the controlled atmosphere. Hence, sensor may be calibrated without disrupting the operation of the workstation.

The automatic control means may comprise an operator activation button to initiate the calibration of the sensor when actuated by the operator.

The automatic control means may comprise a time lapse activation to automatically initiate calibration of the sensor after a predetermined time period. Alternatively or additionally, the automatic control means may comprise a time lapse activation to identify the sensor requires calibration after a predetermined time period and activate an operator warning. The operator warning may be a light, message or any other suitable means for warning the operator that calibration is required. The predetermined time period for the time lapse activation may depend on the type of sensor, the type of controlled atmosphere and/or the use of the workstation.

The calibration system comprises enclosure means movable between a first position and a second position; and a mechanism, operable by the automatic control means, for moving the enclosure means between the first position and the second position.

In the first position, the enclosure means is spaced from the sensor by a predetermined distance such that the sensing head is exposed in the controlled atmosphere of the workstation. As a result, the sensor is able to monitor the gas concentration of the controlled atmosphere. In the first position, the enclosure means may be regarded as being in a fully open position. The enclosure member may at least partially extend into a workspace chamber of the workstation when arranged in the first position. Alternatively, the enclosure means may be arranged within a recess or roofspace of the workstation.

In the second position, the enclosure means is arranged in engagement with at least one further surface so as to define a calibration chamber and enclose the sensing head within the calibration chamber. The sensing head is thereby cut-off from the controlled atmosphere of the workstation and so the sensor monitors the atmosphere within the calibration chamber. In the second position, the enclosure means may be regarded as being in a fully closed position.

The enclosure means may comprise a vessel having a cavity in which the sensing head can be received and a cavity edge for engagement with a surface encircling the sensor. The vessel may have any suitable shape. For example, the vessel may be a hollow cylinder having a closed bottom and open top. Alternatively, the enclosure means may comprise a panel-like member for engagement with a housing in which the sensor is located.

The enclosure means may comprise a seal to enhance the engagement with the at least one further surface.

The mechanism for moving the enclosure means between the first position and the second position may comprise a piston, shaft or any other suitable drive means to drive the enclosure means between the first position and the second position. The piston may be a pneumatic piston. The shaft may be driven by an electric motor. The mechanism may comprise a bias to the first position. For example, the mechanism may comprise a spring bias to bias the enclosure means towards the first position.

The calibrating system comprises a gas supply line, operable by the automatic control means, for supplying gas into the calibration chamber to calibrate the sensing scale of the sensor. The gas supply line sequentially supplies at least one gas with a predetermined gas concentration to the calibration chamber such that at least one gas concentration reference point can be determined to calibrate the sensing scale of the sensor.

The gas supply line is configured to flush with at least a first gas with a first predetermined gas concentration through the calibration chamber. Under the control of the automatic control means, the sensor is configured to monitor the first gas such that a first gas concentration reference point for the sensing scale can be determined in accordance with the sensor response to the first gas concentration.

To provide two-point calibration, the gas supply line may be further configured to flush through the calibration chamber with a second gas having a second predetermined gas concentration. Likewise, under the control of the automatic control means, the sensor is configured to monitor the second gas and a second gas concentration reference point for the sensor scale can be determined in accordance with the sensor response to the second gas concentration.

The first and second gas predetermined gas concentrations may be selected to establish a minimum and maximum sensing scale range for the sensor. If the sensor is an oxygen sensor, the first gas may be a gas with a known low or zero oxygen concentration. For example, the first gas may be nitrogen with 0% oxygen content. The second gas may be a gas with a known higher oxygen concentration. For example, the second gas may be ambient air with a 20.9% oxygen content. Hence, calibration system calibrates the oxygen sensor to have a calibrated sensing scale range from 0% to 20.9% oxygen concentration.

A second aspect of the present invention relates to an automated method for calibrating a sensor in-situ in a controlled atmosphere workstation.

The automated method comprising:
arranging an enclosure means to define a calibration chamber in which a sensing head of the sensor is enclosed;
flushing a first gas with a first predetermined gas concentration through the calibration chamber;
monitoring the sensor response to the first gas; and
calibrating a first gas concentration reference point on a sensing scale of the sensor in accordance with the sensor response to the first gas.

The arranging of the enclosure means may comprise the moving of the enclosure means from a first position to a second position using a mechanism under the control of automatic control means; wherein in the first position, the enclosure means is spaced from the sensing head and the sensing head is exposed to the controlled atmosphere of the workstation; and wherein in the second position, the enclosure means engages at least one further surface to define the calibration chamber and enclose the sensing head within the calibration chamber.

The flushing of the first gas may comprise using a gas supply line under the control of automatic control means to supply the first gas under pressure to the calibration chamber.

The monitoring and calibrating may be controlled by automatic control means.

The method may further comprise:
flushing through the calibration chamber a second gas with a second predetermined gas concentration;
monitoring the sensor response to the second gas; and
calibrating a second gas concentration reference point on the sensor scale in accordance with the sensor response to the second gas.

The flushing of the second gas may comprise using a gas supply line controlled by automatic control means to supply the second gas under pressure to the calibration chamber.

The monitoring and calibrating may be controlled by automatic control means.

The method may further comprise:
initiating calibration when an operator activation button is actuated.

The method may further comprise:
moving of the enclosure means from the second position to the first position using the mechanism under the control of the automatic control means when the sensor has been calibrated; and
reinstating sensing of the controlled atmosphere of the workstation.

BRIEF DESCRIPTION OF THE DRAWINGS

Embodiments of the invention will now be described with reference to the accompanying drawings, in which.

DETAILED DESCRIPTION

Figure 1:
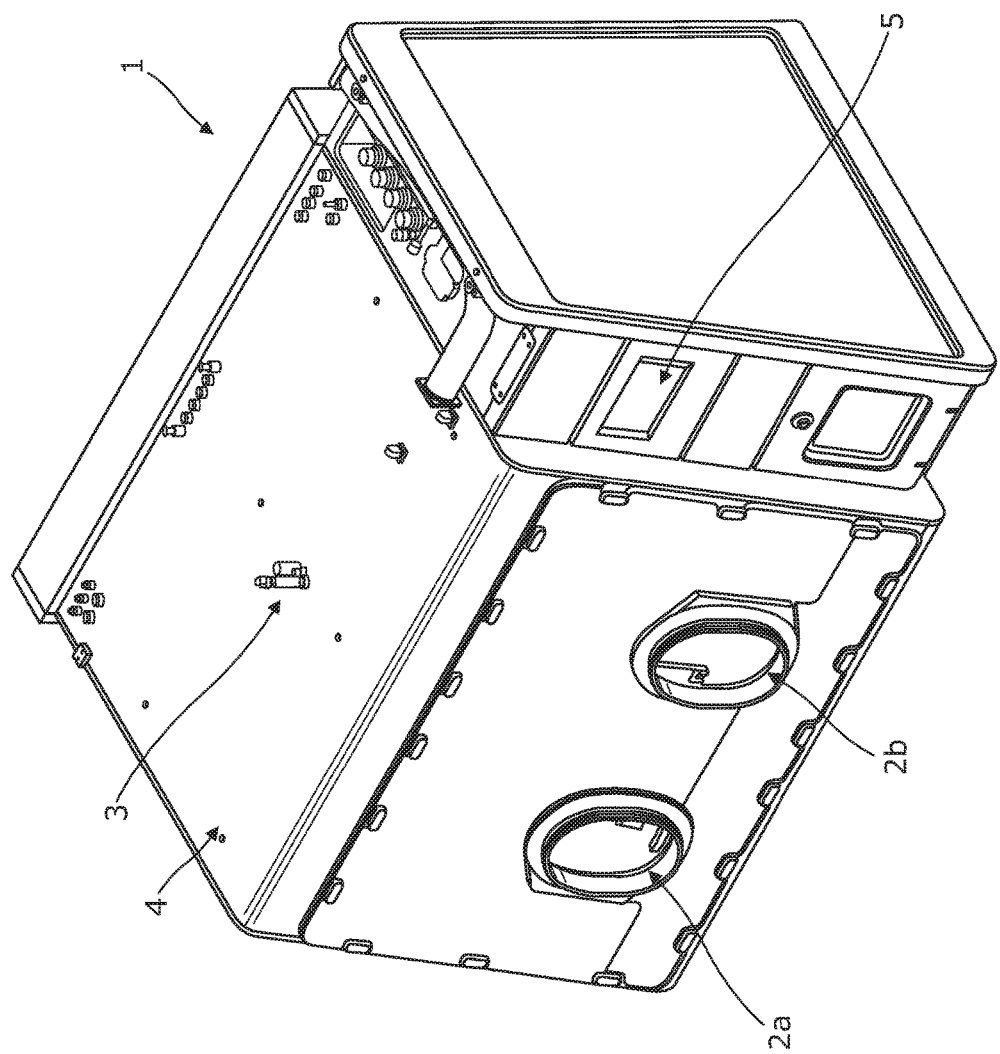
FIG. 1 is a perspective, cut-away view of an embodiment of a workstation according to the present invention with an oxygen sensor.
Figure 2:
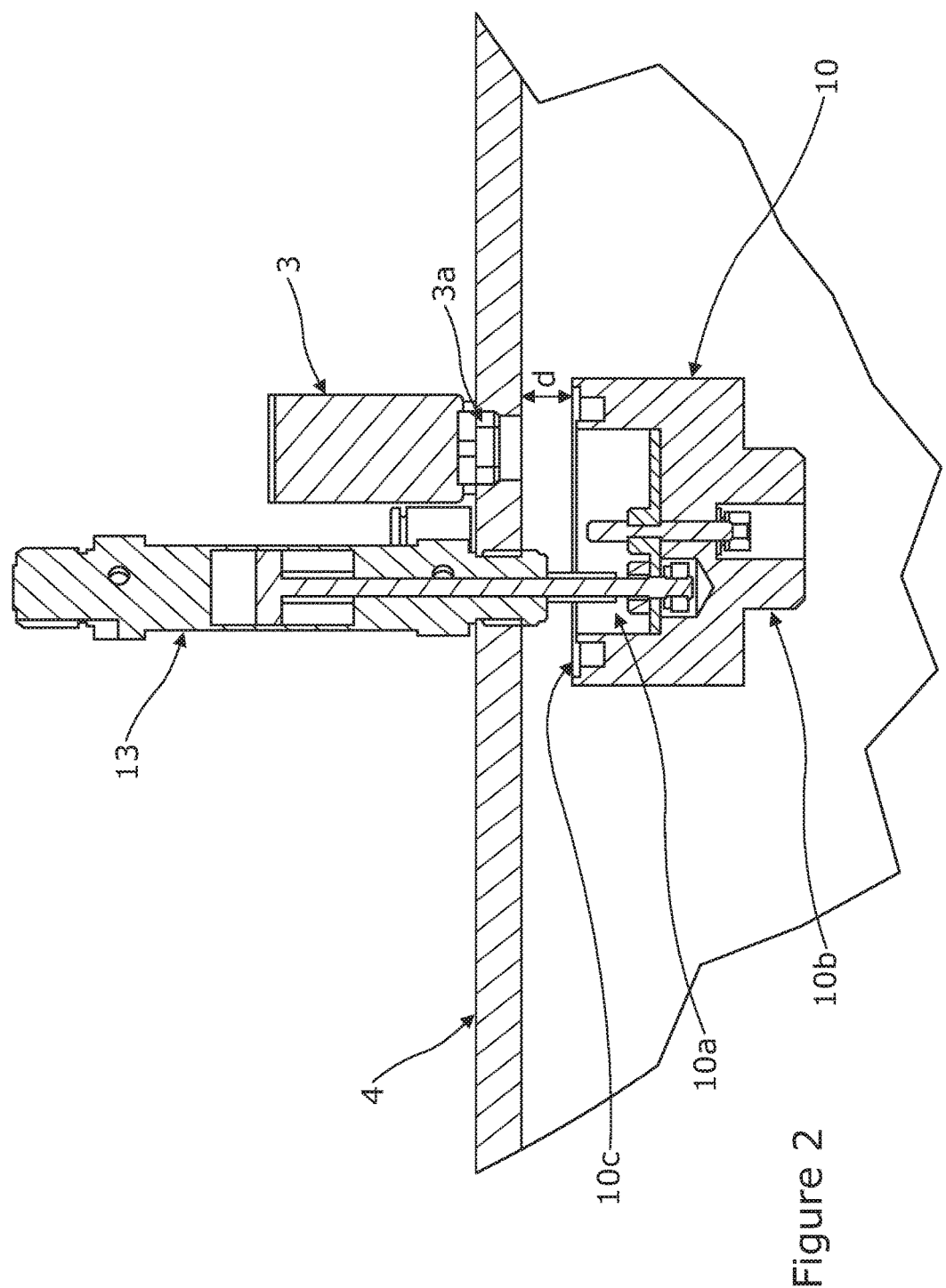
FIG. 2 is a front, schematic view showing an enclosure means of an embodiment of the calibration system according to the present invention arranged in a first position.
Figure 3:
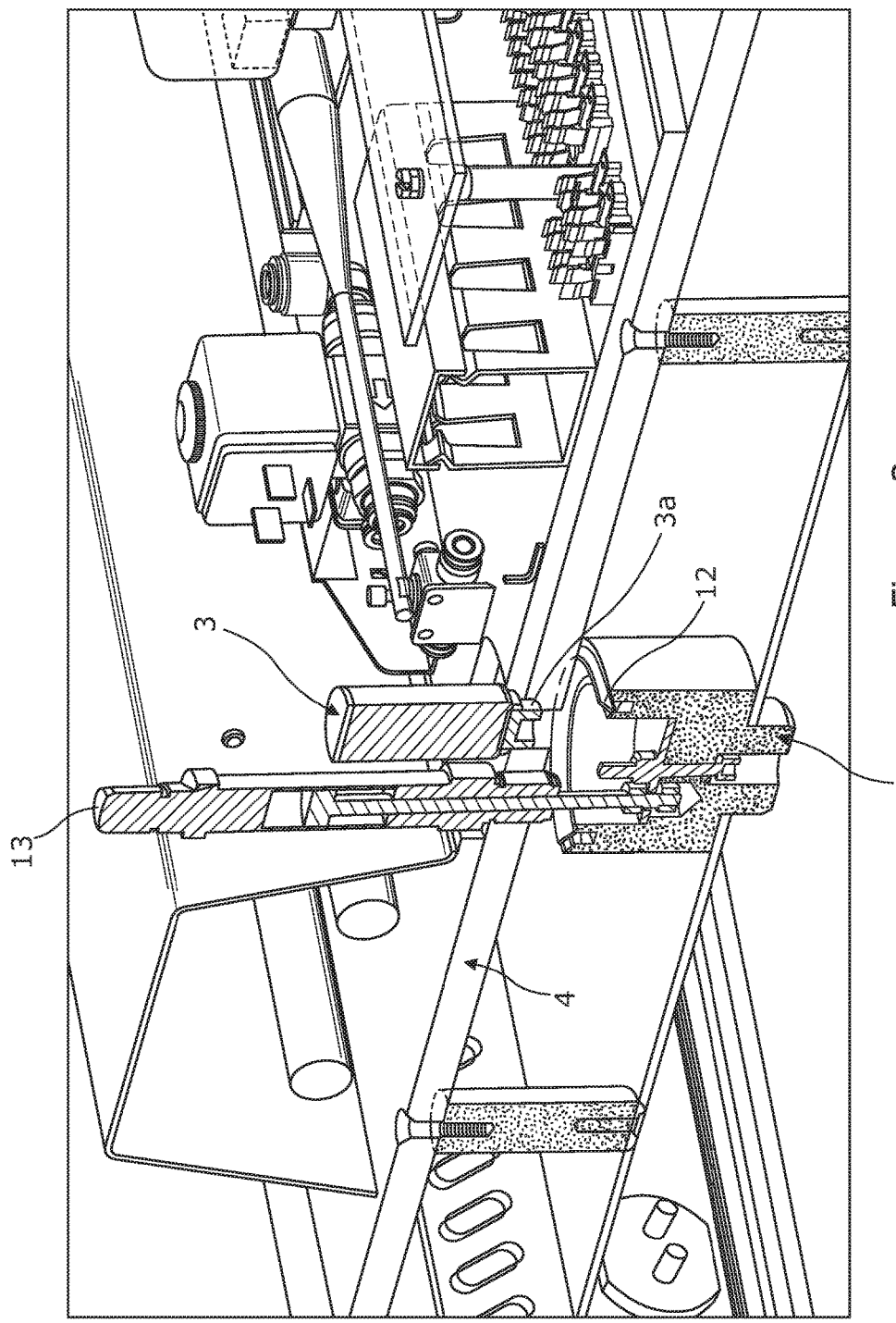
FIG. 3 is a perspective, isometric view showing the enclosure means in the first position.
Figure 4:
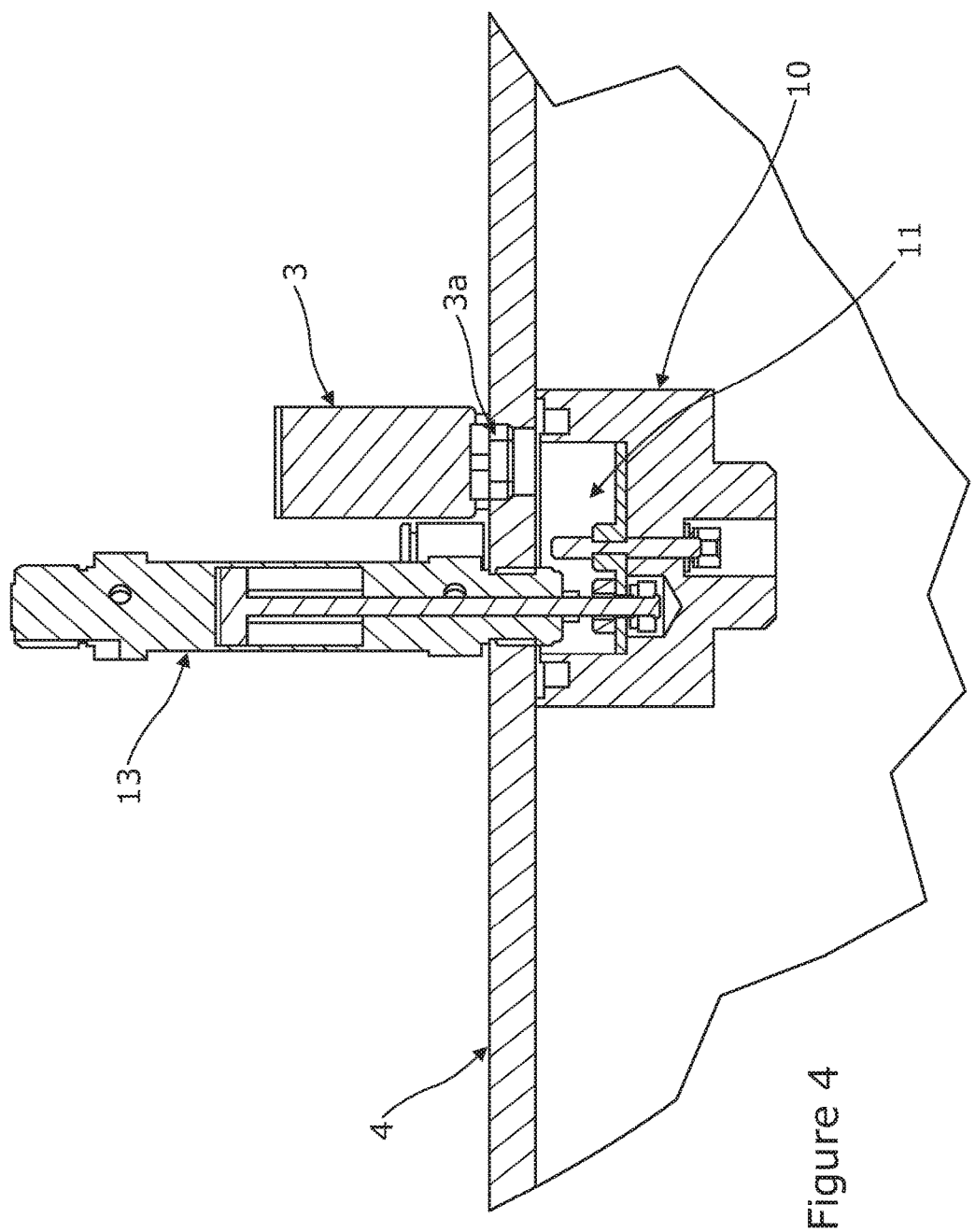
FIG. 4 is a front, schematic view showing the enclosure means of the embodiment of the calibration system in FIGS. 2 and 3 arranged in a second position.
Figure 5:
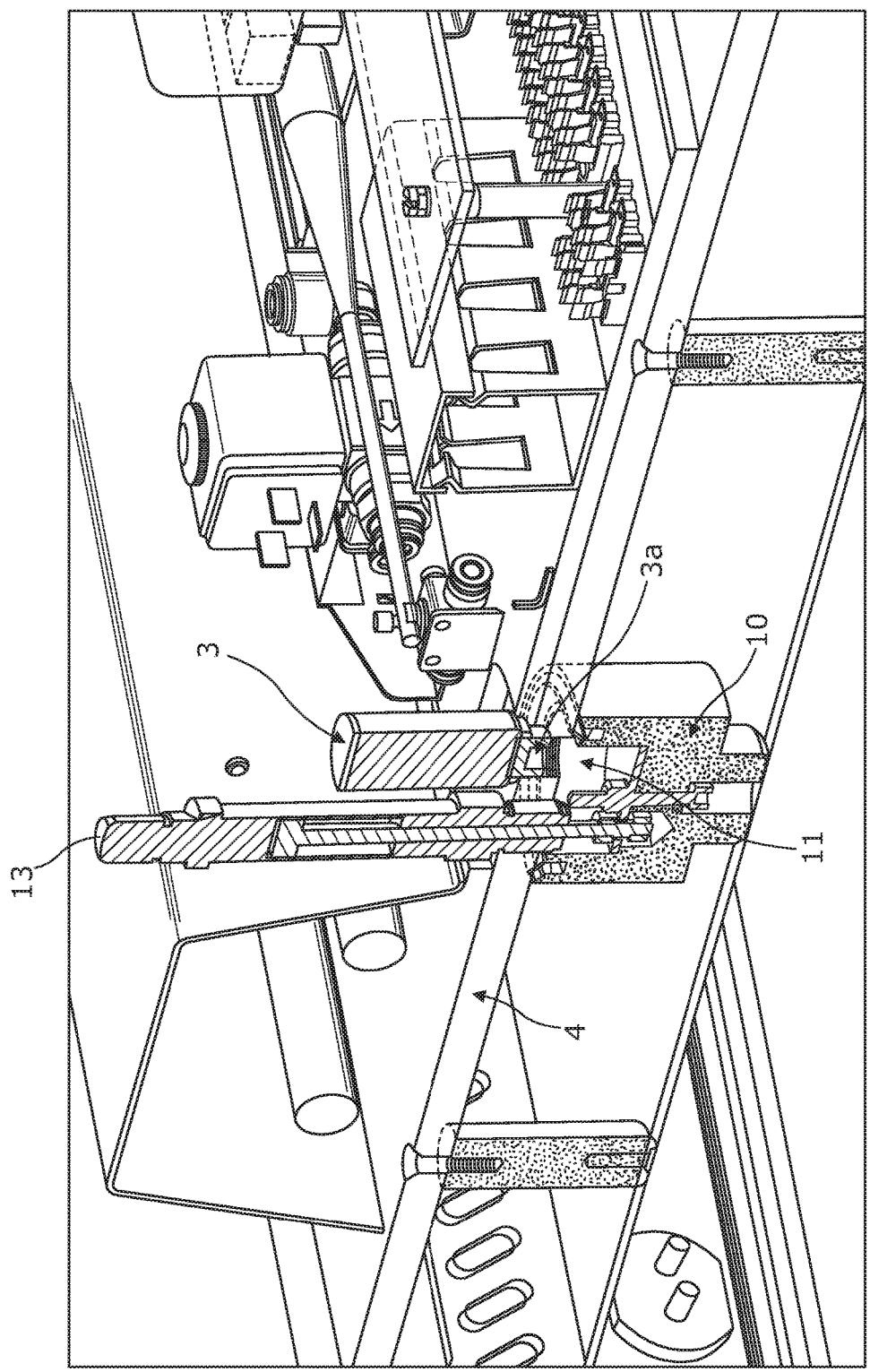
FIG. 5 is a perspective, isometric view showing the enclosure means in the second position.

Referring firstly to FIG. 1, there is shown in general terms an embodiment of a controlled atmosphere workstation 1 according to the present invention. The workstation comprises an internal working chamber in which samples, products, devices can be held under specific atmospheric conditions and in which operations can be carried out. The workstation comprises at least one porthole, preferably a pair of portholes 2a, 2b, through which an operator can insert his arms into the working chamber. The workstation comprises numerous atmosphere control means to control the atmosphere within the working chamber. The atmosphere control means control at least the chemical composition of the atmosphere to provide a particular controlled atmosphere.

In the embodiment depicted in FIG. 1, the atmosphere control means control the oxygen concentration to provide an anaerobic atmosphere in the working chamber. The workstation includes at least one gas sensor to monitor the chemical composition of the atmosphere. In the embodiment depicted in FIG. 1, the workstation comprises an oxygen sensor 3 with a sensing head 3a to monitor the oxygen concentration of the atmosphere in the working chamber. The gas sensor is preferably mounted on the topside of the working chamber as shown in FIG. 1. The sensing head 3a protrudes through an aperture in an upper wall 4 of the working chamber so that it is exposed to the atmosphere in the working chamber. The rear of the gas sensor is preferably protected by a lid of the workstation.

In normal operation of the workstation, the oxygen sensor continuously monitors the concentration of oxygen present in the controlled atmosphere and compares the sensed concentration to an operator-selected value. Additional oxygen and/or other gases may be introduced on demand so as to maintain the controlled atmosphere with the operator-selected oxygen concentration.

To counteract sensor deterioration, the present invention provides a calibration system and method for automatically calibrating at least one gas sensor arranged in-situ in a controlled atmosphere workstation.

FIGS. 2 to 5 depict an embodiment of a calibration system that is configured to calibrate the oxygen sensor mounted in the controlled atmosphere workstation shown in FIG. 1.

The calibration system comprises microprocessor control means to automate the calibration process and minimise, preferably exclude, operator involvement.

In the embodiment depicted in FIGS. 2 to 5, the calibration system includes a button to activate calibration. The button may be incorporated as part of a display, for example the display 5 of the workstation. The microprocessor is configured to initiate calibration of the oxygen sensor when an operator actuates the button.

To avoid any deterioration in performance, the microprocessor is configured to activate a warning after a certain time period has lapsed to warn the operator that the sensor requires calibration. The warning may be a warning message that appears on the display 5 and is removed when the operator actuates the calibration activation button.

To inform the operator, the microprocessor may be further configured to activate a message on the display 5 to indicate the status of the calibration process, when the calibration process is completed and when the workstation is ready for use again.

The microprocessor may additionally or alternatively be pre-programmed to automatically calibrate the oxygen sensor after a certain time period has lapsed, preferably in good time before the accuracy of the sensor degrades.

To allow the sensor to remains in-situ during the calibration process and not compromise the controlled atmosphere in the working chamber, the calibration system comprises a vessel 10 that is arrangeable to enclose the sensing head 3a. The vessel is movable between a first position and a second position as shown in FIGS. 2 to 5.

In the first position, the vessel 10 is spaced a certain distance d from the sensing head 3a in an "open position". As a result, the sensing head 3a is exposed and it is able to monitor the controlled atmosphere of the workstation under normal operating conditions.

In the second position, the vessel 10 is arranged in engagement with the upper wall 4, enclosing the sensing head 3a of the oxygen sensor in a calibration chamber 11. When engaging the wall, the vessel is deemed to be in a "closed position". The sensor is isolated from the controlled atmosphere of the workstation and so monitors the oxygen content of the atmosphere in the calibration chamber.

In the embodiment depicted, the vessel 10 is a cylinder like vessel with an internal cavity space 10a, closed bottom 10b and open top 10c. A circumferential seal 12 extends around the top edge of the cylinder to enhance the engagement with the upper wall surface. When the vessel and upper wall engage, the cavity of the cylinder and upper wall surface define the calibration chamber 11.

The calibration system comprises a mechanism 13 to move the vessel 10 between the first and second positions. In the embodiment depicted, the mechanism is a pneumatic piston operable by the microprocessor. The mechanism is spring loaded to bias the vessel in the first position. During calibration, the microprocessor is configured to control the pneumatic actuation of the piston so as to move the vessel from the first position to the second position and then allow the vessel 10 to return to the first position once the sensor has been calibrated.

The calibration system comprises a gas supply line to supply gas into the calibration chamber to calibrate the oxygen sensor. The operation of the gas supply line is controlled by the microprocessor.

In the embodiment depicted, the gas supply line is configured to initially supply pressurised nitrogen with a 0% oxygen concentration to flush out the calibration chamber. Under the control of the microprocessor, the 0% oxygen concentration sensed by the sensor is calibrated as a minimum oxygen concentration for the sensing scale of the sensor.

After calibrating the 0% oxygen concentration reference point, the gas supply line is further configured to supply pressured ambient air with a 20.9% oxygen content to flush out the calibration chamber. Under the control of the microprocessor, the 20.9% oxygen concentration sensed by the sensor is subsequently calibrated as a maximum oxygen concentration for the sensing scale of the sensor.

After calibrating the sensor, the microprocessor actuates the mechanism to move the vessel back to the first position and the sensing of the oxygen concentration of the controlled atmosphere is reinstated.

Although the invention has been described above with reference to one or more preferred embodiments, it will be appreciated that various changes or modifications may be made without departing from the scope of the invention as defined in the appended claims.

The invention claimed is:

1. An automated calibration system for calibrating a gas sensor in-situ within a controlled atmosphere workstation, the system comprising:
   a controller configured for automatically controlling the calibration system;
   an enclosure member movable between a first position and a second position;
   a drive mechanism, operable by the controller, for moving the enclosure member between the first position and the second position;
   wherein in the first position the enclosure member is arranged in a spaced relationship from the sensor such that a sensing head of the sensor is exposed to the controlled atmosphere of the workstation; and
   in the second position the enclosure member is arranged in engagement with at least one surface so as to define a calibration chamber and enclose the sensing head in the calibration chamber without compromising the controlled atmosphere, wherein the sensing head is isolated from the controlled atmosphere.

2. A system according to claim 1, wherein the enclosure member comprises a vessel with a cavity in which the sensing head can be received and a cavity edge for engagement with a surface encircling the sensor.

3. A system according to claim 1, wherein the drive mechanism comprises a pneumatic piston and/or a motor driven shaft.

4. A system according to claim 1, further comprising a gas supply line, operable by the controller, and configured to sequentially supply at least one gas with a predetermined gas concentration into the calibration chamber such that at least one gas concentration reference point can be determined to calibrate a sensing scale of the sensor.

5. A system according to claim 4, wherein:
the gas supply line is configured to flush a gas with a first gas concentration through the calibration chamber;
the sensor is configured to monitor the first gas concentration under control of the controller; and
the controller is configured to determine a first gas concentration point for the sensing scale of the sensor in accordance with the sensor response to the first gas concentration.

6. A system according to claim 5, wherein:
the gas supply line is configured to flush a gas with a second gas concentration through the calibration chamber; and
the sensor is configured to monitor the second gas concentration under control of the controller; and
the controller is configured to determine a second gas concentration point for the sensing scale of the sensor in accordance with the sensor response to the second gas concentration.

7. A system according to claim 6, wherein the gas sensor comprises an oxygen sensor.

8. A system according to claim 7, wherein the gas with the first gas concentration is nitrogen with 0% oxygen concentration.

9. A system according to claim 8, wherein the gas with the second gas concentration is ambient air with 20.9% oxygen concentration.

10. A system according to claim 1, wherein the controller comprises an operator activation button to initiate the calibration of the sensor when actuated by the operator.

11. A system according to claim 1, wherein the controller comprises a time lapse activation to automatically initiate calibration of the sensor after a predetermined time period.

12. A system according to claim 1, wherein the controller comprises a time lapse activation to identify the sensor requires calibration after a predetermined time period and activate an operator warning.

13. A controlled atmosphere workstation comprising a gas sensor and calibration system for automatically calibrating the gas sensor in-situ according to claim 1.

14. An automated method for calibrating a gas sensor in-situ within a controlled atmosphere workstation, the method comprising:
arranging an enclosure member in a second position so as to define a calibration chamber in which a sensing head of the gas sensor is enclosed;
flushing a gas with a predetermined first gas concentration through the calibration chamber without compromising the controlled atmosphere, wherein the sensing head is isolated from the controlled atmosphere;
monitoring the sensor response to the first gas concentration; and
calibrating a first gas concentration reference point on a sensing scale of the sensor in accordance with the sensor response to the first gas concentration.

15. The method according to claim 14, wherein the arranging of the enclosure member comprises:
moving the enclosure member from a first position to the second position using a mechanism under automatic control;
wherein in the first position, the enclosure member is spaced from the sensing head and the sensing head is exposed to the controlled atmosphere of the workstation; and
wherein in the second position, the enclosure member engages at least one further surface to define the calibration chamber and enclose the sensing head within the calibration chamber.

16. The method according to claim 14, wherein the flushing of the gas with the first gas concentration comprises using a gas supply line under automatic control to supply the gas under pressure to the calibration chamber.

17. The method according to claim 14, wherein the monitoring and calibrating are controlled by automatic control.

18. The method according to claim 14, further comprising:
flushing a gas with a second gas concentration through the calibration chamber; monitoring the sensor response to the second gas concentration; and
calibrating a second gas concentration reference point on the sensor scale in accordance with the sensor response to the second gas concentration.

19. The method according to claim 18, wherein the flushing of the gas with a second gas concentration comprises using a gas supply line controlled by automatic control to supply the second gas under pressure to the calibration chamber.

20. The method according to claim 18, wherein the monitoring and calibrating are controlled by automatic control.

21. The method according to claim 14, further comprising:
initiating calibration when an operator activation button is actuated.

22. The method according to claim 14, further comprising:
moving the enclosure member from the second position to the first position using the mechanism under automatic control when the sensor has been calibrated; and
reinstating the sensing of a gas in controlled atmosphere of the workstation.

* * * * *